United States Patent
Royer

(10) Patent No.: US 9,089,609 B2
(45) Date of Patent: *Jul. 28, 2015

(54) BIORESORABLE POLYMER MATRICES AND METHODS OF MAKING AND USING THE SAME

(71) Applicant: ROYER BIOMEDICAL, INC., Frederick, MD (US)

(72) Inventor: Garfield P. Royer, Upperville, VA (US)

(73) Assignee: ROYER BIOMEDICAL, INC., Frederick, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 14/191,396

(22) Filed: Feb. 26, 2014

(65) Prior Publication Data

US 2014/0248298 A1   Sep. 4, 2014

Related U.S. Application Data

(63) Continuation of application No. 13/867,929, filed on Apr. 22, 2013, now Pat. No. 8,664,280, which is a continuation of application No. 13/228,267, filed on Sep. 8, 2011, now Pat. No. 8,435,565, which is a continuation of application No. 11/983,454, filed on Nov. 9, 2007, now Pat. No. 8,039,021, which is a continuation of application No. PCT/US2006/002380, filed on May 26, 2006.

(60) Provisional application No. 60/684,974, filed on May 27, 2005.

(51) Int. Cl.

| A61K 47/36 | (2006.01) |
| A61K 9/00 | (2006.01) |
| A61K 9/06 | (2006.01) |
| A61K 9/12 | (2006.01) |
| A61K 9/70 | (2006.01) |
| A61K 47/10 | (2006.01) |
| A61L 27/34 | (2006.01) |
| A61L 27/54 | (2006.01) |
| A61L 27/58 | (2006.01) |

(52) U.S. Cl.
CPC ............... *A61K 47/36* (2013.01); *A61K 9/0019* (2013.01); *A61K 9/0024* (2013.01); *A61K 9/06* (2013.01); *A61K 9/12* (2013.01); *A61K 9/7007* (2013.01); *A61K 47/10* (2013.01); *A61L 27/34* (2013.01); *A61L 27/54* (2013.01); *A61L 27/58* (2013.01); *A61L 2300/402* (2013.01); *A61L 2300/406* (2013.01); *A61L 2300/41* (2013.01); *A61L 2300/414* (2013.01); *A61L 2300/416* (2013.01); *A61L 2300/426* (2013.01); *A61L 2300/438* (2013.01); *A61L 2300/602* (2013.01); *A61L 2300/64* (2013.01)

(58) Field of Classification Search
None
See application file for complete search history.

(56) References Cited

U.S. PATENT DOCUMENTS

| 3,988,411 A | 10/1976 | Capozza |
| 6,133,325 A | 10/2000 | Schwartz et al. |
| 6,326,018 B1 | 12/2001 | Gertzman et al. |
| 6,790,840 B1 | 9/2004 | Lee et al. |
| 7,030,093 B2 | 4/2006 | Vogt et al. |
| 2005/0002893 A1 | 1/2005 | Goldmann |
| 2005/0118230 A1 | 6/2005 | Hill et al. |

FOREIGN PATENT DOCUMENTS

| WO | 95/34328 | 12/1995 |
| WO | 97/41899 | 11/1997 |
| WO | 2004/112713 | 12/2004 |

OTHER PUBLICATIONS

Yoshitani et al, Microscale Synthesis of Dextran-Based Multivalent N-Linked Oligosaccharide Probes, Analytical Biochemistry, 277:127-134, 2000.
Supplemental European Search Report, EP 06 77 1261, dated Nov. 10, 2010.
Balakrishnan et al, Biomaterioals, 2004, vol. 26, pp. 3941-3951.
Bouhadir et al, Polymer, 1999, vol. 40, pp. 3575-3584.
Chegel et al, J Biochem. Biophys. Methods, 2002, vol. 50, pp. 201-216.
Hennink et al, Advanced Drug Delivery Review, 2002, vol. 54, pp. 13-36.
Search results, google scholar, Jun. 21, 2013.

*Primary Examiner* — Kade Ariani
(74) *Attorney, Agent, or Firm* — Nixon & Vanderhye P.C.

(57) ABSTRACT

Bioactive agents are delivered to a body site in need of the same by providing a first aliquot portion of a reaction mixture which includes an aldehydic polymer solution, and a second aliquot portion of a reaction which includes a cross-linking hydrazide and a bioactive agent. The first and second aliquot portions may be mixed (e.g., by expelling such portions from respective syringe barrels) to form the reaction mixture thereof. The thus formed reaction mixture may then be installed at the body site whereby the reaction mixture is allowed to solidify in situ within about 1 to 10 minutes into a reaction product comprised of a hydrazide cross-linked oxidized aldehydic polymer matrix with the bioactive agent entrapped therein.

21 Claims, No Drawings

BIORESORABLE POLYMER MATRICES AND METHODS OF MAKING AND USING THE SAME

CROSS-REFERENCE

This application is a continuation of commonly owned U.S. Ser. No. 13/867,929, filed Apr. 22, 2013 (U.S. Pat. No. 8,664,280) which is a continuation of U.S. Ser. No. 13/228,267, filed Sep. 8, 2011 (U.S. Pat. No. 8,435,565) which is a continuation of U.S. Ser. No. 11/983,454, filed on Nov. 9, 2007 (U.S. Pat. No. 8,039,021), which is a continuation of PCT/US2006/02380, filed May 26, 2006, which is based on and claims domestic priority benefits under 35 USC §119 (e) from U.S. Provisional Application Ser. No. 60/684,974, filed May 27, 2005, the entire content of each application being hereby incorporated by reference.

FIELD OF INVENTION

The present invention relates generally to bioresorbable polymer matrices and to their production and use as delivery systems for bioactive agents. Sustained and/or controlled release of pharmaceuticals and other bioactive agents, including cells, are the primary uses of the matrices of the present invention.

BACKGROUND AND SUMMARY OF THE INVENTION

Polymer matrices designed for controlled release of bioactive compounds can be non-resorbable or resorbable. In general, resorbable means biologically degradable in the body by erosion from the surface of breakdown from within. The mechanism can involve either a chemical reaction, such as hydrolysis, or dissolution. Non-resorbable polymers, such as polymethylmethacrylate, have been used for antibiotic delivery. These materials suffer from the disadvantage that they must be retrieved, which involves a second intervention and entails the risk of infection (H W Bucholz, et al., (1970) Chiburg, 43, 446).[1]

[1] This publication as well as other publications cited hereinbelow are expressly incorporated in their entirety into this application.

Preparation of oxidized dextran is described in U.S. Pat. No. 5,783,214 to Royer. Oxidized hyaluronic acid has been used in reactions with amino polysaccharides to form complexes as described in U.S. Pat. No. 6,305,585 to Spiro et al; however, the disclosed method is less convenient and more expensive compared to the system described herein. Also, the cross-linking conditions require uncharged amino groups, which eliminates many active ingredients, as they would react with the polymer. The gel described in U.S. Pat. No. 6,305,585 is prepared in bulk by reacting two polymer solutions at alkaline pH. Lee et al, Macromolecules, 33, 97-101 (2001), have described a structural biomaterial made of poly(gulur-onate), which involves an oxidized polymer isolated from alginic acid. The starting material is not commercially available, is expensive to produce, and has not been FDA-approved for medicinal use. The production of this biomaterial occurs at high pH that would involve reaction of amino groups in proteins or of other medicinal compounds.

Another polysaccharide that finds application in medicine is carboxymethylcellulose used in drug formulation and also the production of anti-adhesion compositions for post-surgical treatment following several types of procedures (Schwartz H E and Blackmore J M, U.S. Pat. Nos. 6,017,301, 6,133,325, and 6,034,140; Miller M E, Cortese, S M, Schwartz, H E and Oppelt, W G, U.S. Pat. No. 6,566,345; Llu, L S and Berg, R, U.S. Pat. No. 6,923,961; Schwartz, H W, Blackmore, J M, Cortese, S M, and Oppelt, W G, U.S. Pat. No. 6,869,938). These formulations involve the non-covalent aggregation of carboxylated polysaccharides with polyethyleneglycols.

Hyaluronic acid has been used as a biomaterial for a number of applications, Gertzman and Sunwoo have employed the sodium salt of high molecular weight hyaluronic acid to deliver demineralized bone matrix (U.S. Pat. Nos. 7,019,192; 6,911,212; 6,458,375 and 6,328,018). The material used is a solution and does not involve chemical cross-linking as described herein. The covalent cross-linking provides for gel stability and retards migration of the bioactive agent. Also, the degree of cross-linking constitutes an element of control for the residence time/resorption rate.

In contrast to some of the polymers cited in the above references, dextran employed in the practice of the present invention is available as a USP product and has been used parenterally for many years. Acrylate derivatives of dextran have been produced and can form cross-linked hydrogels (De Groot et al, (2002) Int. J. Cancer, 98, 134-140; Stenekes, et al. (2000) Biomacromolecules, 1, 696-703; Chung, et al. (2005) Int. J. Pharm., 288, 51-61). Polylactide-dextran grafts can be produced and employed to make a delivery matrix using an emulsion based microsphere system (Quchi, et al. (2004) 4, 455-463)

Commonly owned international Patent Publication No. WO 2004/112712 discloses novel drug polymer complexes, which are formed by mixing a polyanion such as dextran sulfate sodium and a cationic bioactive agent. The resulting resorbable gels (R Gels) or precipitate constitutes a drug delivery matrix. As disclosed, however, there are only ionic bonds involved in the formation of such R Gels. Furthermore, the formation of such R Gels requires that the active pharmaceutical ingredient must be positively charged. Many active ingredients, however, are neutral or negatively charged at physiological pH. The carbohydrate matrix of R Gels is very attractive in that it is polar and not susceptible to proteolytic degradation.

It would therefore be highly desirable if the resorbable polymer systems were able to deliver neutral or negatively charged active ingredients at physiological pH. It is towards providing such resorbable polymer systems that the present invention is directed.

Broadly, the present invention disclosed herein entails the usage of chemically modified polysaccharides in the preparation of delivery matrices for drug molecules, which are not usable with conventional R Gels, included are negatively charged and neutral active ingredients. In especially preferred embodiments, the matrix involves cross-linking of aldehydic polymers with dihydrazides in the presence of an active ingredient. The cross-linking reagent, the dihydrazide, reacts to form a hydrazone. A film, microbeads, or rubbery solid is the product of the reaction.

According to one aspect of this invention, bioerodible compositions for delivery of a bioactive agent are provided which are the reaction products of a reaction mixture comprised of an oxidized dextran solution, and a mixture of solids comprised of a dihydrazide, a bioactive agent, and optionally a pH adjusting agent in an amount sufficient to achieve a pH of the reaction mixture of 6 or less. Preferably the pH of the reaction mixture will be 6 or less whether or not a pH adjusting agent is employed. If employed, however, preferred pH adjusting agents are solid acids, such as sodium phosphate, citric acid, succinic acid and/or fumaric add.

The compositions of the invention may further comprise a release agent for controlling release of the bioactive agent from the composition. One preferred form of the release agent is a complexing polymer which binds to the bioactive agent. Alternatively or additionally, the release agent may comprise a non-reactive matrix polymer to provide structural stability and diffusional resistance to the bioactive agent, In some preferred embodiments of the invention, the release agent will comprises an aliphatic or aromatic acid which forms salts with aminoglycoside antibiotics, vancomycin, tetracyclines or clindamycin.

Virtually any bioactive agent may be employed satisfactorily in the present invention. In this regard, preferred bioactive agents comprise osteoinductive agents, antibiotics, anesthetics, growth factors, cells, anti-tumor agents, anti-inflammatory agents, antiparasitics, antigens, adjuvants and cytokines. One particularly preferred bioactive agent is an osteoinductive agent, such as demineralized bone matrix (DBM).

The compositions of the invention may be provided in the form of a gel, microsphere, film, foam, or fiber.

According to another aspect of this Invention, kits for forming a bioerodible composition adapted for delivery of a bioactive agent are provided. The kits of the invention will comprise a first aliquot portion of a reaction mixture comprised of an oxidized dextran solution, and a second aliquot portion of a reaction mixture comprised of a mixture of solids which include a dihydrazide, a bioactive agent, and optionally a pH adjusting agent in an amount sufficient to achieve a pH of the reaction mixture of 6 or less. When mixed the first and second aliquot portions of the reaction mixture react to form a solidified bioerodible composition for delivery of the bioactive agent contained therein. The release agent, if employed, may therefore be incorporated into one of the first and second aliquot portions of the reaction mixture.

The kits of the invention may advantageously be provided with a double syringe having first and second syringe barrels which respectively contain the first and second aliquot portions of the reaction mixture.

According to yet another aspect of the invention, methods of making a solidified bioerodible composition for delivery of a bioactive agent are provided. The preferred methods comprise forming a reaction mixture comprised of an oxidized dextran solution, and a mixture of solids comprised of a dihydrazide, a bioactive agent, and optionally a pH adjusting agent in an amount sufficient to achieve a pH of the reaction mixture of 6 or less, and allowing the reaction mixture to react to form a solidified bioerodible drug delivery composition.

Several systems may be employed to prepare the resorbable polymer matrix according to the invention for administration. For example, it is possible to connect two syringes physically one to another and to effect mixing of the reactable components by reciprocating action no as to transfer the mixture repetitively from one syringe barrel, to another. The pH is held at 6 or below to prevent reaction of amino groups on the active ingredient. The bioactive agent, dihydrazide, and solid acid (all dry powders) are contained in the first syringe and the oxidized dextran solution in the in second syringe. There are many advantages to this format including stability of the bioactive agent, maintenance of sterility, and convenience.

In yet another aspect, the present invention is embodied. In implantable medical device which comprises a coating of the solidified bioerodible composition. The medical devices may advantageously be in the form of a catheter, a stent or an orthopedic device. Particularly preferred coated orthopedic devices in accordance with the present invention include pins, screws, rods, nails, wires, augments, cups, and joint implants.

According to yet another aspect of the present invention, methods of delivering a bioactive agent to a body site in need of the same are provided. The methods comprise providing a first aliquot portion of a reaction mixture comprising an oxidized dextran solution, and a second aliquot portion of a reaction mixture comprising a mixture of solids comprised of a dihydrazide, a bioactive agent, and optionally a pH adjusting agent in an amount sufficient to achieve a pH of the reaction mixture of 6 or less. The first and second aliquot portions may be mixed together to form the reaction mixture, so that subsequently, the reaction mixture may be installed at the body site and allowed to form a solidified bioerodible drug delivery composition to be formed thereby in situ. A double syringe having first and second syringe barrels which respectively contain the first and second aliquot portions of the reaction mixture may be provided. The step of expelling the first and second aliquot portions of the reaction mixtures may therefore be practiced by repeatedly transferring the first and second aliquot portions of the reaction mixtures between the first and second syringe barrels so as to mix the same.

These and other aspects and advantages will become more apparent after careful consideration is given to the following detailed description of the preferred exemplary embodiments thereof.

DETAILED DESCRIPTION OF THE INVENTION

The components necessarily required to producing the polymer complexes of the present invention include an bioactive agent, an aldehydic polymer, and a multifunctional hydrazide. Mixing the above components results in a solid matrix as a consequence of the reaction of dihydrazide with the aldehyde groups on the polymer chains with three dimensional cross-linking. The reaction is run at acid pH (e.g., between about 4.0 to about 6.0) In order to speed the gel formation and to prevent reaction of amino groups of the active ingredient. The active ingredient is thus trapped within the resulting polymer matrix. Shortly after mixing the components the solution/suspension is infected/installed in an animal or human patient. The matrix solidifies in situ within several minutes (e.g., usually within about 5 minutes). The hydrated polymer matrix degrades in viva and is therefore resorbable by the body. Unlike polyesters no acid is produced as a result of resorption.

Non-reactive polymers may be included to alter the diffusional resistance or to complex the bioactive agent.

In general, the ideal drug delivery matrix displays the following characteristics:

1. Non-toxic
2. Resorbable
3. Versatile as to molecular size and chemical nature of the bioactive agent
4. No requirement far exotic components that are expensive or difficult to obtain
5. Controllable release rate
6. Producible according to GMP at reasonable cost
7. Sterilizable Disclosed herein are polysaccharide drug delivery matrices and the methodology for producing and using the same. More specifically, the polysaccharide drug delivery matrices of the present invention may be derived from periodate-oxidized dextran and dihydrazides. The cross-linking reaction is carried out at acidic pH, which allows entrapment of bioactive substances with free amino groups. Protonation of the amino groups in the pH range of 4-6 renders such groups relatively unreactive as compared to the dihydrazides. Hence the bioactive agent remains in tact and does not consume aldehydic cross-linking sites.

It is important to maintain the pH of the reaction mixture to between about 4.0 to about 6.0. In some cases, it may be necessary to add an agent, such as sodium phosphate or an organic acid (e.g., citric or fumaric acid), to adjust the pH to within the desired range. In the cases where the active ingredients are present as salts, the addition of sodium phosphate or an organic acid to adjust the pH is not always necessary, in general; therefore, when the active ingredient contributes acidity, there may not be a need to add an acidic agent so as to adjust the pH.

Vicinol diols react with sodium metaperiodate to yield aldehydes. Polyglucans, mannans, levans, and the like, react smoothly in aqueous solution at room temperature. When a polymer such as dextran is reacted with periodate the result is iodate and a polymer chain containing intermittent dialdehyde groupings. These dialdehydes serve as sites for reaction with adipic dihydrazide, which results in the formation of a covalently cross-linked hydrophilic gel.

The reaction to form the polymer complexes according to the present invention may be represented schematically as:

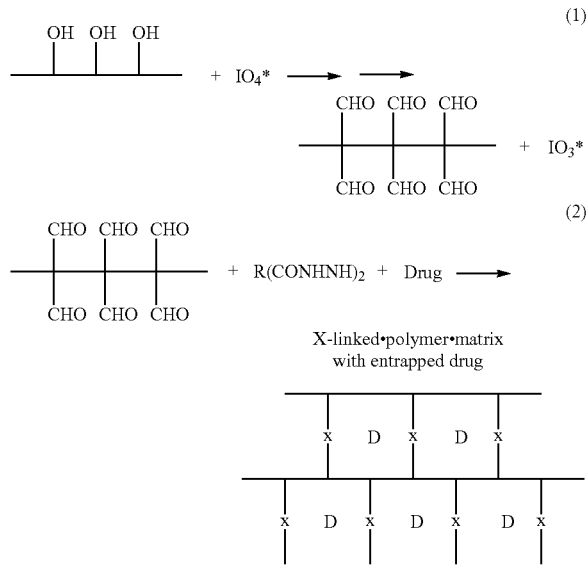

in which X represents the dihydrazone cross-link and D represents the active ingredient. It should be stressed that only a fraction of the vicinol diols in the polysaccharide are reacted. On a residue molar basis, the degree of oxidation is in the 5-20% range. The reaction scheme above is not intended to represent stoichiometry of the reaction.

Release rate and control of the release profile are important considerations of drug delivery systems.

Fick's Law of diffusion states that:

$$Rate = DA(\partial c/\partial x)$$

where D is the diffusion coefficient; A is the surface area and ($\partial c/\partial x$) is the concentration gradient at the boundary of the matrix.

To paraphrase the Stokes-Einstein equation, D can be expressed as:

$$D = kS/M_w V$$

in which k is a constant, S is the solubility of the active ingredient, $M_w$ is the molecular weight and V is the viscosity of the medium. Complexation can reduce the effective solubility and the addition of non-reactive polymers can increase the "viscosity" or diffusional resistance. The oxidation level may be varied from between about 5% to about 20%. The polymer concentration can be within the range of between about 50 to about 250 mg/ml depending on the system employed for preparing the formulation. Active ingredients can be converted to hydrophobic salts. For instance, amines can be converted with C6 or greater carboxylic acids. These salts can be employed to extend the release profile either alone or in combination with highly soluble inorganic salts.

The polymers to be oxidized must be biocompatible and resorbable. Any polymer that meets these criteria may be used. Preferred are dextran (produced by microbial fermentation) and derivatives thereof; dextrans from other sources may be employed as long as they are biocompatible and have properties similar to USP dextran. The preferred molecular weight of the polymer is 40,000 or greater. In general, the reaction time required for gellation is longer when low molecular weight oxidized dextran is employed.

The cross-linking hydrazides that are useful include the following:

| Carbon No. | Name |
|---|---|
| C4 | Succinic adid dihydrazide |
| C5 | Glutaric acid dihydrazide |
| C6 | Adipic acid dihydrazide |
| C7 | Pimelic acid dihydrazide |
| C8 | Suberic acid dihydrazide |
| C9 | Azalaic acid dihydrazide |
| C10 | Sebacic acid dihydrazide |
| C11 | Undecanedioic acid dihydrazide |
| C12 | Dodecanedioic acid dihydrazide |
| C13 | Brassylic acid dihydrazide |
| C14 | Tetradecanedioic acid dihydrazide |
| C15 | Pentadecanedioic acid dihydrazide |
| C16 | Thapsic acid dihydrazide |
| C18 | Octadecanedioic acid dihydrazide |

Organic solvent-water mixtures can be used to accelerate dissolution and reaction rates when higher molecular weight hydrazides are employed.

The matrices described herein are usefully employed for delivering bioactive agents including, for example, drugs, hormones, cytokines, growth factors, cells, and the like. Direct injection for local or systemic drug delivery is one mode of use. Others include coatings for implants, wound sealant, topical wound dressing, local installation perioperatively for infection control or pain control (local anesthetic).

One embodiment of the present invention includes demineralized bone matrix (DBM) which is made by treating donor bone with acid to remove the inorganic components (Urist, M R, et al., Proc. Natl. Acad. Sci. (1984) 81, 372-375; Peterson, et al., JBJS (2004) 86, 2243-2250). Following sterilization, DBM can be mixed with a carrier and placed in an orthopedic defect. Osteoinduction results in new bone formation.

DBM can be delivered to an orthopedic defect using the matrix described herein in at least two ways. First, the DBM dry solid can be blended with the dihydrazide and subsequently treated with oxidized dextran solution. The resulting liquid suspension is taken up in a syringe and installed by the surgeon. With most forms of DBM, the dual syringe system can be employed.

Secondly, the mixture containing polymer matrix and DBM is allowed to solidify. When dry, this material becomes quite hard and will bear weight. The dry composite is then fashioned to form the desired shape. Cancellous bone chips, hydroxyapatite, or other inorganic materials may be included in the formulation prior to installation.

Those skilled in the art will of course recognize that it is possible to combine other bioactive agents with the osteoinductive DBM. A DBM/antibiotic matrix may therefore be useful for treating bone and joint infections.

Furthermore, a DBM/bupivacaine matrix may be useful for treating pain at bone graft procurement sites, such as the iliac crest, which is a common source for allograft bone for use in spine arthrodesis.

For a number of orthopedic applications, bone marrow aspirate is another logical additive to use with osteoinductive DBM with the matrix described herein.

Mesenchymal stem cells and other progenitor cells may be delivered with regulatory biochemicals. Chondrocytes may be delivered for repair of articular cartilage.

One additional beneficial use of the matrices according to the present invention is the prevention of post-surgical adhesions. Specifically, following surgery (such as abdominal, gynecological, or pelvic surgery) the installation of a matrix in accordance with the present invention may contribute to the significant reduction of adhesions. Various adjuvants can be employed including fibrinolytic agents, anticoagulants, anti-inflammatory agents, and antibiotics. In this application an additional polymer such as polyethyleneglycol (8000) is advantageously included in the oxidized dextran solution.

A duel syringe set-up may be used in preparation of the resorbable polymer matrices according to the present invention. For example a solution of an aldehydic polymer, such as oxidized dextran, may be contained within the barrel of one syringe, while a mixture of solid drug and solid dihydazide may be contained within the barrel of the other syringe. Monosodium phosphate may be included to control pH, which is advantageously maintained in the range of between about 4.0 to about 6.0. The syringes are connected to one another so that the contents may be mixed by alternately transferring the mixture from one syringe barrel to another for about 30 cycles. Solidification occurs within about 1 to about 10 minutes depending on the relative concentrations of components. The oxidized dextran solution is stable for at least one year and the solid components are stable for at least that time, in some cases indefinitely. Maintenance of sterility, broad applicability, stability of the bioactive agent and ease of use are the attributes of such a double syringe system.

Various physical forms of the invention may be produced. In this regard, it is especially preferred that the polymer matrices of the invention be in the form of an injectable liquid, which solidifies inside the body. The injectable liquid made with the double syringe system can also be applied to surgical wounds/incisions or the wounds resulting from injuries. The formulation solidifies and serves as a wound sealant. Antibiotics and growth factors may be used to prevent infection and promote healing.

Another approach is to allow the dosage form to set up (solidify) ex vivo prior to being administered. After drying and milling, the resulting powder can be used topically. Alternatively or additionally, the powder can be suspended and used parenterally.

A solid dosage form of the invention solidified ex vivo may be used as a topical anti-infective powder for wound treatment. Entrapment of clindamycin and amikacin within a resorbable polymer matrix produces a broad spectrum, long lasting antibiotic powder. Other types of antibiotics such as fluoroquinolones, glycopeptides, macrolides, beta lactams and others can also be employed either singly or in combination as may be desired.

Fibers of the resorbable polymer matrices according to the present invention can be prepared by injection spinning of the reaction mixture into isopropanol.

These fibers may be tailored by changing the relative amount of cross-linking reagent and/or the use non-reactive polymers. The fibers containing antibiotic can be woven into a bandage or used as is to treat an infection such as a septic diabetic foot ulcer.

Microbeads are readily prepared using oxidized dextran and dihydrazides. After mixing using the double syringe the formulation is injected into rapidly stirred mineral oil containing a surfactant. The resulting microbeads are washed with organic solvent, dried, and packaged. These microbeads are suspendable in water and can be injected through a 23-gauge needle.

The utility of the invention is further illustrated by the non-limiting entries shown in Table 1.

TABLE 1

Illustrative applications of the invention.

| Indication | Dosage Form | Bioactive Agent |
|---|---|---|
| Orthopedic Defects | Injectable gel or Implantable solid | DBM or other osteoinductive agent |
| Localized Infections | Injectable gel, film, microspheres, fibers | Tobramycin Clindamycin |
| Pain Control | Injectable gel or microspheres | Bupivacaine |
| Regional Nerve Blocks | Injectable gel or microspheres | Bupivacaine |
| Cancer | Injectable gel or microspheres | Carboplatin Paciltaxel |
| Vaccine | Injectable gel or microspheres | Antigen, adjuvant |

The present invention will be further understood after careful consideration is given to the following non-limiting examples thereof.

EXAMPLES

Example 1

Preparation of Oxidized Dextran

Dextran (4 g; Mw 500,000) was dissolved in 20 ml distilled water. To this solution was added 535 mg of finely ground $NaIO_4$ with rapid stirring. The mixture was stirred in the dark for 1 hour and then dialyzed against three changes of distilled water (1 L each). The oxidized dextran solution (about 70 mg/ml) was stored at room temperature in the dark. The solution was concentrated with a rotary evaporator at 40° C. to about 200 mg/ml.

Example 2

Ciprofloxacin/Clindamycin Matrix

Oxidized dextran solution, prepared as described in Example 1 (1 ml, 93 mg/ml), was loaded into a 3 ml syringe. A finely ground powder containing 21 mg adipic dihydrazide, 20 mg citric acid, and 150 mg ciprofloxacin was loaded into a second 3-ml syringe. The syringe, which contained about 0.5 ml of air along with the powder mixture was closed with a plug-type cap.

Just prior to use the two syringes were coupled using a double-ended connector. The contents of the syringes were mixed during about 30 reciprocations. Installation of the mixture into a wound may be accomplished via a needle or oannula attached to the syringe containing the mixture. The setting time for this formulation is 8-10 minutes.

Substitution of a mixture of ciprofloxacin and clindamycin (75 mg each) for ciprofloxacin yields a broad spectrum formulation covering anaerobes as well as aerobes.

Example 3

Preparation of Bupivacaine FE/CMC Matrix

Bupivacaine (100 mg) was placed into a mortar and ground with 100 mg carboxymethylcellulose sodium (CMC) ($M_w$ 70,000). Oxidized dextran ($M_w$, 500,000; 66 mg/ml; 1 ml) was blended with the bupivacaine/CMC mixture at room temperature. After a homogenous suspension was obtained, adipic acid dihydrazide (7.8 mg) was added. A sample (200 mg) of the resulting gel was transferred to a 2 ml centrifuge tube for the release experiment in PBS buffer. The release profile of the formulation appears in Table 1 below:

TABLE 1

| Day | % Release/Day |
| --- | --- |
| 1 | 10 |
| 2 | 10 |
| 3 | 10 |
| 4 | 9 |
| 5 | 5 |
| 6 | 5 |
| 7 | 5 |
| 8 | 3 |

Example 4

Preparation of Bupivacaine FB/Dextran Sulfate Sodium (DSS) Matrix

Bupivacaine FB (100 mg) was finely ground with 50 mg DSS (Mw, 500,000). Oxidized dextran solution (Mw, 500,000; 66 mg/ml; 1 ml) was added to the bupivacaine-DSS powder and mixed at room temperature. To the resulting homogenous suspension adipic acid dihydrazide (7.8 mg) and succinic acid (10 mg) were added. A sample (200 mg) of the reaction mixture was transferred into a 2 ml centrifuge tube for the release experiment in PBS buffer. The release profile of the matrix appears in Table 2 below:

TABLE 2

| Day | % Release/Day |
| --- | --- |
| 1 | 11 |
| 2 | 10 |
| 3 | 9 |
| 4 | 7 |
| 5 | 7 |
| 6 | 7 |
| 7 | 6 |
| 8 | 4 |

Example 5

Preparation of Piperacillin Matrix

Piperacillin (sodium salt, 50 mg) was placed in 5 ml beaker. Oxidized dextran solution (Mw, 500,000; 85 mg/ml; 1 ml) was added to the piperacillin and mixed thoroughly at room temperature. After a homogenous suspension was created, adipic acid dihydrazide (10 mg) was added and mixed thoroughly. A sample (200 mg) of the resulting formulation was transferred to a 2 ml centrifuge lube for the release experiment in PBS buffer. The release profile of the matrix appears in Table 3 below:

TABLE 3

| Day | % Release/Day |
| --- | --- |
| 1 | 42 |
| 2 | 28 |
| 3 | 21 |
| 4 | 8 |

Example 6

Preparation of Ceftlofur Matrix

Ceftlofur-HCl (50 mg) and adipic acid dihydrazide (10 mg) were placed in a 1-ml syringe. This syringe was connected to a second syringe containing 1 ml of oxidized dextran (Mw, 500,000; 85 mg/ml; 1 ml). The contents of the two syringes were mixed by making 20 reciprocations. A sample (200 µl) of the reaction mixture was transferred to a 2 ml centrifuge tube for the release experiment in PBS buffer. The release profile of the matrix appears in Table 4 below:

TABLE 4

| Day | % Release/Day |
| --- | --- |
| 1 | 2.5 |
| 2 | 2.5 |
| 3 | 2.9 |
| 4 | 3.0 |
| 5 | 3.2 |
| 6 | 3.5 |
| 7 | 4.0 |

Example 7

Preparation Azoalbumin Matrix

Sodium phosphate (40 mg) was dissolved in 1 ml of oxidized dextran solution (Mw, 500,000; 66 mg/ml). Azoalbumin (30 mg) was added and mixed thoroughly at room temperature. After homogenous suspension was created adipic acid dihydrazide (8 mg) was added. After about one hour, 200 mg of the resulting complex was transferred into a centrifuge lube for the release experiment in PBS buffer. The release profile of the matrix appears in Table 5 below:

TABLE 5

| Day | % Release/Day |
| --- | --- |
| 1 | 25 |
| 2 | 14 |
| 3 | 13 |
| 4 | 10 |
| 5 | 8 |
| 6 | 7 |
| 7 | 6 |
| 8 | 5 |
| 9 | 4 |
| 10 | 3 |

TABLE 5-continued

| Day | % Release/Day |
|-----|---------------|
| 11  | 3             |
| 12  | 3             |

Example 8

Formulation of Amikacin/Demineralized Bone Matrix (DBM)

Amikacin Sulfate (100 mg), DBM (200 mg), and 8 mg of adipic acid dihydrazide were placed into a beaker and mixed thoroughly. Oxidized dextran solution (Mw, 500,000; 66 mg/ml; 1 ml) was added to the mixture. Tobramycin-sulfate or tobramycin-sulfate/clindamycin-HCl (1/1) can be used in place of amikacin-sulfate.

Example 9

Preparation of Paclitaxel Matrix

Paclitaxel (30 mg) was finely ground with 40 mg of monosodium phosphate and 30 mg adipic dihydrazide. The resulting powder was transferred to a 3 ml syringe fitted with a Luer plug. The syringe was connected to a second syringe containing 3 ml of oxidized dextran (Mw, 500,000; 85 mg/ml). After about thirty reciprocations of the syringe plungers, the gel was ready to inject. The liquid mixture may therefore be installed in the cavity left by lumpectomy where it gels in situ. The paclitaxel may kill cancer cells on the margins of the cavity and also serves as a radiation sensitizer during adjuvant radiation.

Example 10

Preparation of Vancomycin Matrix

Vancomycin (100 mg) was finely ground with 30 mg DSS (Mw, 500,000) and 8 mg adipic dihydrazide. The mixture was loaded into a 3-ml syringe fitted with a Luer plug. Oxidized dextran solution (1 ml, Mw of 500,000; 66 mg/ml) was loaded into a second syringe. An injectable formulation was formed after connecting the syringes and performing 30 reciprocations of the syringe plungers.

Example 11

Preparation of Doxycycline Matrix

Doxycycline-HCl (100 mg) was finely ground with 90 mg DSS (Mw, 500,000) and 8 mg adipic dihydrazide. The mixture was loaded into a 3-ml syringe fitted with a Luer plug. Oxidized dextran solution (1 ml, Mw of 500,000; 66 mg/ml) was loaded into a second syringe. An injectable formulation was formed after connecting the syringes and performing 30 reciprocations of the syringe plungers.

Example 12

Preparation of Antibiotic Foam

One syringe contains a polymer solution-oxidized dextran (70,000 Mw, 10% oxidation, 160 mg/ml) and carboxymethylcellulose (medium viscosity, 16 mg/ml). The second syringe contains 15 mg of adipic dihydrazide, 50 mg ciprofloxacin, and 30 mg of an effervescent mixture, which consisted of 1.2 g sodium bicarbonate and 1 g of citric acid. The syringes were connected and the contents mixed by 20 reciprocations. This antibiotic foam is advantageously used in treatment of wounds which are infected or are likely to become infected.

Example 13

Preparation of a Moldable Gels and Films

One syringe contains oxidized dextran (70,000 Mw, 160 mg/ml, and 10% oxidation) and carboxymethylcellulose (medium viscosity, sodium salt, 16 mg/ml). The second syringe contains adipic dihydrazide (15 mg) and 50 mg ciprofloxacin. The syringes were connected and the contents mixed and expressed after 20 reciprocations. Starch glycolate (sodium salt, 30 mg) can be substituted for carboxymethylcellulose. These formulations can be quickly spread to cast a film. The alternative is to shape them after an acceptable plasticity is attained prior to installation into a defect or application to a wound.

Example 14

Preparation of Carboxylic Acid Salts of Aminoglycoside Antibiotics

Amikacin (586 mg) was suspended in 10 ml of 80% methanol. Octanoic acid (700 µl) was added with stirring. The mixture was stirred for 3 hours at room temperature. The solvent was evaporated and the residue was triturated with hexane. A solid resulted with a melting point of 105-110° C. Using a stoichiometry of 4 acid to 1 amikacin other salts can be made using this procedure. Examples include hexanoate and laurate. Similarly, hexanote, octanoate, and laurate salts of tobramycin, and gentamycin have been prepared in accordance with the procedures of this Example 13.

Example 16

Preparation of Carboxylic Acid Salts of Clindamycin

Clindamycin (460 mg) was dissolved in 5 ml of 80% methanol. Lauric acid (200 mg) was added with stirring. The mixture was stirred for 2 hours at room temperature and then concentrated with a rotary evaporator. Trituration with 10 ml of hexane yielded a solid. After drying in vacuo overnight the melting point was found to be 103-105° C. Other useful salts include hexanoate and octanoate. Lincomycin salts can be prepared in a similar fashion.

Example 16

Preparation of Carboxylic Acid Salts of Bupivacaine

Bupivacaine (576 mg) was dissolved in 7 ml of 80% methanol. To this stirred solution was added 316 µl of caprylic acid. After two hours at room temperature, the mixture was concentrated using a rotary evaporator. The resulting solid had a melting range of 90-96° C. Hexanoate and laurate salts can be prepared in a similar manner.

Example 17

Preparation of Doxycycline Matrix

Doxycycline (100 mg) was finely ground and mixed with 6 mg adipic dihydrazide. This mixture was loaded into a 3-ml syringe fitted with a Luer plug. Oxidized dextran solution (1 ml, Mw of 500,000; 110 mg/ml) was loaded into a second syringe. An injectable formulation was formed after connecting the syringes and performing 30 reciprocations of the syringe plungers.

Example 18

Preparation of Antibiotic Coated Implants

Tobramycin caprylate (50 mg) and clindamycin caprylate (50 mg) were ground together. This solid mixture was loaded into Syringe A (3 ml) with 10 mg of adipic dihydrazide. A solution of oxidized dextran (1 ml; Mw 70,000; 10% oxidation; 100 mg/ml) was loaded into Syringe B (3 ml). A femoral stem was pre-heated to 60° C. Syringe A and Syringe B were connected and the contents mixed with 20 reciprocations of the syringe plungers. Using a brush and one the syringes fitted with a blunt cannula, the implant was coated with homogenous layer of material. After drying overnight, the coated implant was immersed in a tube containing phosphate buffered saline (PBS) at 37° C. The eluate showed antibacterial activity for more than one week.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of delivering a bioactive agent to a body site in need of the same, comprising the steps of:
    (i) providing a first aliquot portion of a reaction mixture comprising an aldehydic polymer solution, and a second aliquot portion of a reaction mixture comprising a cross-linking hydrazide and a bioactive agent;
    (ii) mixing the first and second aliquot portions to form the reaction mixture thereof; and
    (iii) installing the reaction mixture at the body site and allowing the reaction mixture to solidify in situ within about 1 to 10 minutes into a reaction product comprised of a hydrazide cross-linked oxidized aldehydic polymer matrix with the bioactive agent entrapped therein.

2. The method of claim 1, wherein step (i) includes providing a double syringe having first and second syringe barrels which respectively contain the first and second aliquot portions of the reaction mixture.

3. The method of claim 2, wherein step (ii) includes expelling the first and second aliquot portions of the reaction mixtures from the first and second syringe barrels, respectively.

4. The method of claim 3, wherein step (ii) includes repeatedly transferring the first and second aliquot portions of the reaction mixtures between the first and second syringe barrels so as to mix the same.

5. The method according to claim 1, wherein the bioactive agent is at least one selected from the group consisting of osteoinductive agents, antibiotics, anesthetics, growth factors, cells, anti-tumor agents, anti-inflammatory agents, anti-parasitics, antigens, adjuvants and cytokines.

6. The method according to claim 1, wherein the bioactive agent is an osteoinductive agent which comprises demineralized bone matrix (OBM).

7. The method according to claim 1, wherein the bioactive agent is an antibiotic.

8. The method according to claim 7, wherein the antibiotic is gentamycin.

9. The method of claim 1, wherein the aldehydic polymer has a molecular weight of 40,000 or greater.

10. The method of claim 1, wherein the aldehydic polymer is oxidized dextran.

11. The method as in claim 1, wherein the reaction mixture has a pH of 4 to 6.

12. The method as in claim 11, which comprises mixing a adjusting agent in an amount sufficient to achieve a pH of the reaction mixture of 4 to 6.

13. The method according to claim 1, wherein the reaction product is in the form of a gel, microsphere, film, foam, or fiber.

14. A method of delivering an antibiotic to a body site in need of the same, comprising the steps of:
    (i) providing a first aliquot portion of a reaction mixture comprising an aldehydic polymer solution in a first syringe barrel, and a second aliquot portion of a reaction mixture comprising a cross-linking hydrazide and an antibiotic in a second syringe barrel;
    (ii) mixing the first and second aliquot portions by expelling the first and second aliquot portions of the reaction mixtures from the first and second syringe barrels, respectively, to form the reaction mixture thereof; and
    (iii) installing the reaction mixture at the body site and allowing the reaction mixture to solidify in situ within about 1 to 10 minutes into a reaction product comprised of a hydrazide cross-linked oxidized aldehydic polymer matrix with the antibiotic entrapped therein.

15. The method according to claim 14, wherein the antibiotic is gentamycin.

16. The method according to claim 14, wherein step (ii) comprises repeatedly transferring the first and second aliquot portions of the reaction mixtures between the first and second syringe barrels so as to mix the same.

17. The method according to claim 16, wherein the first and second syringe barrels are provided by a double syringe.

18. The method of claim 14, wherein the aldehydic polymer has a molecular weight of 40,000 or greater.

19. The method of claim 18, wherein the aldehydic polymer is oxidized dextran.

20. The method as in claim 14, wherein the reaction mixture has a pH of 4 to 6.

21. The method as in claim 20, which comprises mixing a adjusting agent in an amount sufficient to achieve a pH of the reaction mixture of 4 to 6.

* * * * *